US008436176B2

(12) United States Patent  
Martin et al.

(10) Patent No.: US 8,436,176 B2
(45) Date of Patent: May 7, 2013

(54) PROCESS FOR PREPARING 2-METHYL-1-(2-METHYLPROPYL)-1H-IMIDAZO[4,5-C][1,5]NAPHTHYRIDIN-4-AMINE

(75) Inventors: Hughes Martin, Cergy Pontoise Cedex (FR); David Ach, Cergy Pontoise Cedex (FR); Clement Toussaint, Cergy Pontoise Cedex (FR); Fabrice Dubois, Pithiviers (FR)

(73) Assignee: Medicis Pharmaceutical Corporation, Scottsdale, AZ (US)

( * ) Notice: Subject to any disclaimer, the term of this patent is extended or adjusted under 35 U.S.C. 154(b) by 907 days.

(21) Appl. No.: 11/794,584

(22) PCT Filed: Dec. 18, 2005

(86) PCT No.: PCT/US2005/047375  
§ 371 (c)(1),  
(2), (4) Date: Jul. 14, 2008

(87) PCT Pub. No.: WO2006/074046  
PCT Pub. Date: Jul. 13, 2006

(65) Prior Publication Data  
US 2008/0306266 A1      Dec. 11, 2008

Related U.S. Application Data

(60) Provisional application No. 60/641,129, filed on Dec. 30, 2004, provisional application No. 60/708,679, filed on Aug. 16, 2005.

(51) Int. Cl.  
*C07D 515/00*      (2006.01)  
*A61K 31/44*      (2006.01)

(52) U.S. Cl.  
USPC ............................................. 546/82; 514/293

(58) Field of Classification Search ........................ None  
See application file for complete search history.

(56) References Cited

U.S. PATENT DOCUMENTS

| | | |
|---|---|---|
| 3,314,941 A | 4/1967 | Littell et al. |
| 3,764,681 A | 10/1973 | Dreikorn |
| 3,917,624 A | 11/1975 | Abu El-Haj et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster et al. |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,693,811 A | 12/1997 | Lindstrom |
| 5,741,908 A | 4/1998 | Gerster et al. |
| 5,756,747 A | 5/1998 | Gerster |
| 5,922,884 A | 7/1999 | Huang et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,107,322 A | 8/2000 | Huang et al. |
| 6,110,929 A | 8/2000 | Gerster et al. |
| 6,194,425 B1 | 2/2001 | Gerster et al. |
| 6,245,776 B1 | 6/2001 | Skwierczynski et al. |
| 6,331,539 B1 | 12/2001 | Crooks et al. |
| 6,376,669 B1 | 4/2002 | Rice et al. |
| 6,433,002 B2 | 8/2002 | Huang et al. |
| 6,451,810 B1 | 9/2002 | Coleman et al. |
| 6,514,985 B1 | 2/2003 | Gerster et al. |
| 6,518,265 B1 | 2/2003 | Kato et al. |
| 6,518,280 B2 * | 2/2003 | Gerster et al. ............... 514/293 |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,608,093 B2 | 8/2003 | Huang et al. |
| 6,624,172 B2 | 9/2003 | Lindstrom et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,264 B2 | 12/2003 | Dellaria et al. |

(Continued)

FOREIGN PATENT DOCUMENTS

| | | |
|---|---|---|
| EP | 0 394 026 | 10/1990 |
| EP | 1 104 764 | 6/2001 |

(Continued)

OTHER PUBLICATIONS

Lide, D., ed., CRC Handbook of Chemistry and Physics, 71st Edition, 1990 p. 8-46.*  
Wozniak, et al, "The Amination of 3-nitro-1, 5-naphthyridines by Liquid Ammonia/Potassium Permanganate[1,2]. A New and Convenient Amination Method.", Journal of the Royal Netherlands, Chemical Society, 102, pp. 511-513, Dec. 12, 1983.  
Brennan, et al, "Automated Bioassay of Interferons in Micro-test Plates", Biotechniques, Jun./Jul. 1983.  
Testerman, et al., "Cytokine Induction by the Immunomodulators Imiquimod and S-27609", Journal of Leukocyte Biology, vol. 58, pp. 365-372, Sep. 1995.  
Bachman, et al, "Synthesis of Substituted Quinolylamines. Derivatives of 4-Amino-7-Chloroquinoline", J. Org. Chem, 15, pp. 1278-1284 (1950).  
Jain, et al, Chemical and Pharmacological Investigations of Some ω-Substituted Alkylamino-3- aminopyridineso, J. Med. Chem., 11, pp. 87-92 1968.

(Continued)

*Primary Examiner* — D M Seaman  
*Assistant Examiner* — Heidi Reese  
(74) *Attorney, Agent, or Firm* — Medicis Pharmaceutical Corporation

(57) ABSTRACT

The invention provides various processes for preparing 2-methyl-1-(2-methylpropyl)-1H-imidazo[4,5-c][1,5]naphthyridin-4-amine.

66 Claims, No Drawings

U.S. PATENT DOCUMENTS

| | | |
|---|---|---|
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,693,113 B2 | 2/2004 | Lindstrom |
| 6,706,728 B2 | 3/2004 | Hedenstrom et al. |
| 6,743,920 B2 | 6/2004 | Lindstrom et al. |
| 6,747,040 B2 | 6/2004 | Lindstrom et al. |
| 6,756,382 B2 | 6/2004 | Coleman et al. |
| 6,797,718 B2 | 9/2004 | Dellaria et al. |
| 6,818,650 B2 | 11/2004 | Griesgraber |
| 6,894,165 B2 | 5/2005 | Gerster et al. |
| 6,949,646 B2 | 9/2005 | Gerster et al. |
| 2002/0016332 A1 | 2/2002 | Slade |
| 2002/0055517 A1 | 5/2002 | Smith |
| 2002/0110840 A1 | 8/2002 | Tomai et al. |
| 2003/0130299 A1 | 7/2003 | Crooks et al. |
| 2003/0133913 A1 | 7/2003 | Tomai et al. |
| 2003/0139364 A1 | 7/2003 | Krieg et al. |
| 2003/0161797 A1 | 8/2003 | Miller et al. |
| 2003/0199538 A1 | 10/2003 | Skwierczynski et al. |
| 2004/0014779 A1 | 1/2004 | Gorden et al. |
| 2004/0091491 A1 | 5/2004 | Kedl et al. |
| 2004/0132079 A1 | 7/2004 | Gupta et al. |
| 2004/0141950 A1 | 7/2004 | Noelle et al. |
| 2004/0147543 A1 | 7/2004 | Hays et al. |
| 2004/0162309 A1 | 8/2004 | Gorden et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Miller et al. |
| 2004/0181130 A1 | 9/2004 | Miller et al. |
| 2004/0181211 A1 | 9/2004 | Graham et al. |
| 2004/0191833 A1 | 9/2004 | Fink et al. |
| 2004/0192585 A1 | 9/2004 | Owens et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2004/0235881 A1 | 11/2004 | Mitra et al. |
| 2005/0054590 A1 | 3/2005 | Averett |

FOREIGN PATENT DOCUMENTS

| | | |
|---|---|---|
| JP | 9-208584 | 8/1997 |
| JP | 9-255926 | 3/1999 |
| JP | 11-222432 | 8/1999 |
| JP | 2000-247884 | 9/2000 |
| WO | WO 01/74343 | 10/2001 |
| WO | WO 02/36592 | 5/2002 |
| WO | WO 02/46194 | 6/2002 |
| WO | WO 02/46749 | 6/2002 |
| WO | WO 02/102377 | 12/2002 |
| WO | WO 03/020889 | 3/2003 |
| WO | WO 03/043572 | 5/2003 |
| WO | WO 03/045391 | 6/2003 |
| WO | WO 03/097641 | 11/2003 |
| WO | WO 2004/091500 | 10/2004 |

OTHER PUBLICATIONS

Baranov, et al., Chem. Abs. 85, 94362, (1976).

Berényi, et al, "Ring Transformation of Condensed Dihydro-as-triazines", J. Heterocyclic Chem., 18, pp. 1537-1540 (1981).

Chollet, et al, "Development of a Topically Active Imiquimod Formulation", Pharmaceutical Development and Technology, 4(1), pp. 35-43 (1999).

Izumi, et al., "1H-Imidazo[4,5-c]quinoline Derivatives as Novel Potent TNF-a Suppressors: Synthesis and Structure-Activity Relationship of 1-, 2- and 4- Substituted 1H-imidazo[4,5-c]pyridines", Bioorganic & Medicinal Chemistry, 11, pp. 2541-2550 (2003).

Hart, E.P. "Naphthyridines. Hydroxynaphthyridines", Journal of the Chemical Society, Part III, pp. 212-214 (1956).

Wagner, et al., "Induction of Cytokines in Cynomoglus Monkeys by the Immune Response Modifiers, Imiquimod, S-27609 and S-28463", Cytokine, 9(11), pp. 837-845 (1997).

Wermuth, "Molecular Variations Based on Isosteric Replacements", The Practice of Medicinal Chemistry, pp. 203-237 (1996).

* cited by examiner

PROCESS FOR PREPARING 2-METHYL-1-(2-METHYLPROPYL)-1H-IMIDAZO[4,5-C][1,5]NAPHTHYRIDIN-4-AMINE

CROSS-REFERENCE TO RELATED APPLICATION

The present invention is a 35 U.S.C. §371 national stage of PCT application PCT/US2005/047375, filed Dec. 28, 2005, which claims priority to U.S. Provisional Application Ser. No. 60/641,129, filed on Dec. 30, 2004, and to U.S. Provisional Application Ser. No. 60/708,679, filed on Aug. 16, 2005, both of which are incorporated herein by reference in their entirety.

BACKGROUND

The compound 2-methyl-1-(2-methylpropyl)-1H-imidazo[4,5-c][1,5]naphthyridin-4-amine has been found to be a useful immune response modifier (IRM) due to its ability to induce cytokine biosynthesis. However, manufacturing pharmaceutical products can present many unforeseen challenges and new methods of preparation are needed.

SUMMARY OF THE INVENTION

In one aspect, the invention provides a method for preparing 2-methyl-1-(2-methylpropyl)-1H-imidazo[4,5-c][1,5]naphthyridin-4-amine. The method includes: providing 2-methyl-1-(2-methylpropyl)-5-oxido-1H-imidazo[4,5-c][1,5]naphthyridine in a carrier that includes a lower alcohol; combining the 2-methyl-1-(2-methylpropyl)-5-oxido-1H-imidazo[4,5-c][1,5]naphthyridine in the carrier with an ammonia- or ammonium-containing reagent and an arylsulfonyl halide to form a mixture; allowing the components of the mixture to react for a period of time sufficient to form 2-methyl-1-(2-methylpropyl)-1H-imidazo[4,5-c][1,5]naphthyridin-4-amine. Preferably, the method also includes combining the mixture with an aqueous base.

Preferably, providing 2-methyl-1-(2-methylpropyl)-5-oxido-1H-imidazo[4,5-c][1,5]naphthyridine includes: providing 2-methyl-1-(2-methylpropyl)-1H-imidazo[4,5-c][1,5]naphthyridine (referred to above) in a carrier that includes a non-chlorinated solvent at a temperature of 25° C. to 70° C.; combining the 2-methyl-1-(2-methylpropyl)-1H-imidazo[4,5-c][1,5]naphthyridine in the carrier with an oxidizing agent to form a mixture and maintaining the mixture at a temperature of 25° C. to 70° C. for a period of time sufficient to form 2-methyl-1-(2-methylpropyl)-5-oxido-1H-imidazo[4,5-c][1,5]naphthyridine; and isolating at least a portion of the 2-methyl-1-(2-methylpropyl)-5-oxido-1H-imidazo[4,5-c][1,5]naphthyridine.

Preferably, providing 2-methyl-1-(2-methylpropyl)-1H-imidazo[4,5-c][1,5]naphthyridine (referred to above) includes: providing $N^4$-(2-methylpropyl)[1,5]naphthyridine-3,4-diamine in a carrier that includes a non-chlorinated solvent at a temperature of 18° C. to 30° C.; combining the $N^4$-(2-methylpropyl)[1,5]naphthyridine-3,4-diamine in the carrier with an organic acid to form a mixture; combining the mixture that includes the $N^4$-(2-methylpropyl)[1,5]naphthyridine-3,4-diamine and organic acid with a trialkyl orthoacetate at a temperature of 70° C. to 100° C.; and maintaining the temperature at 70° C. to 100° C. for a period of time sufficient to form 2-methyl-1-(2-methylpropyl)-1H-imidazo[4,5-c][1,5]naphthyridine.

Preferably, providing $N^4$-(2-methylpropyl)[1,5]naphthyridine-3,4-diamine (referred to above) includes: providing $N^4$-(2-methylpropyl)-3-nitro[1,5]naphthyridin-4-amine in a carrier that includes a non-chlorinated solvent; combining the $N^4$-(2-methylpropyl)-3-nitro[1,5]naphthyridin-4-amine in the carrier with a hydrogenation catalyst to form a mixture; subjecting the mixture that includes the $N^4$-(2-methylpropyl)-3-nitro[1,5]naphthyridin-4-amine and the hydrogenation catalyst to a hydrogen atmosphere under conditions effective to form $N^4$-(2-methylpropyl)[1,5]naphthyridine-3,4-diamine; and removing at least a portion of the hydrogenation catalyst from the $N^4$-(2-methylpropyl)[1,5]naphthyridine-3,4-diamine.

Preferably, providing $N^4$-(2-methylpropyl)-3-nitro[1,5]naphthyridin-4-amine (referred to above) includes: providing 4-chloro-3-nitro[1,5]naphthyridine in a carrier that includes a water-miscible organic liquid; combining the 4-chloro-3-nitro[1,5]naphthyridine in the carrier with isobutylamine under conditions effective to form a mixture that includes the $N^4$-(2-methylpropyl)-3-nitro[1,5]naphthyridin-4-amine; combining the mixture that includes the $N^4$-(2-methylpropyl)-3-nitro[1,5]naphthyridin-4-amine with water to form solid $N^4$-(2-methylpropyl)-3-nitro[1,5]naphthyridin-4-amine; and separating at least a portion of solid $N^4$-(2-methylpropyl)-3-nitro[1,5]naphthyridin-4-amine from at least a portion of the mixture that includes the water.

Preferably, providing 4-chloro-3-nitro[1,5]naphthyridine (referred to above) includes: providing 3-nitro[1,5]naphthyridin-4-ol in a carrier that includes N,N-dimethylformamide; combining the 3-nitro[1,5]naphthyridin-4-ol in the carrier with phosphorous oxychloride under conditions effective to form 4-chloro-3-nitro[1,5]naphthyridine; combining the mixture that includes the 4-chloro-3-nitro[1,5]naphthyridine with water under conditions effective to form solid 4-chloro-3-nitro[1,5]naphthyridine; and separating at least a portion of the solid 4-chloro-3-nitro[1,5]naphthyridine from at least a portion of the mixture that includes the water.

In a preferred embodiment, providing 2-methyl-1-(2-methylpropyl)-5-oxido-1H-imidazo[4,5-c][1,5]naphthyridine (referred to above) includes: providing 3-nitro[1,5]naphthyridin-4-ol in a carrier including N,N-dimethylformamide; combining the 3-nitro[1,5]naphthyridin-4-ol in the carrier with phosphorous oxychloride under conditions effective to form 4-chloro-3-nitro[1,5]naphthyridine; combining the mixture that includes the 4-chloro-3-nitro[1,5]naphthyridine with water under conditions effective to form solid 4-chloro-3-nitro[1,5]naphthyridine; separating at least a portion of the solid 4-chloro-3-nitro[1,5]naphthyridine from at least a portion of the mixture that includes the water; combining the separated solid 4-chloro-3-nitro[1,5]naphthyridine with a carrier that includes a water-miscible organic liquid; combining the 4-chloro-3-nitro[1,5]naphthyridine in the carrier with isobutylamine under conditions effective to form a mixture that includes $N^4$-(2-methylpropyl)-3-nitro[1,5]naphthyridin-4-amine; combining the mixture that includes the $N^4$-(2-methylpropyl)-3-nitro[1,5]naphthyridin-4-amine with water to form solid $N^4$-(2-methylpropyl)-3-nitro[1,5]naphthyridin-4-amine; separating at least a portion of solid $N^4$-(2-methylpropyl)-3-nitro[1,5]naphthyridin-4-amine from at least a portion of the mixture that includes the water; and converting the solid $N^4$-(2-methylpropyl)-3-nitro[1,5]naphthyridin-4-amine to 2-methyl-1-(2-methylpropyl)-5-oxido-1H-imidazo[4,5-c][1,5]naphthyridine.

In one aspect, the invention provides a method for making $N^4$-(2-methylpropyl)-3-nitro[1,5]naphthyridin-4-amine. The method includes: providing 3-nitro[1,5]naphthyridin-4-ol in a carrier including N,N-dimethylformamide; combining the 3-nitro[1,5]naphthyridin-4-ol in the carrier with phosphorous oxychloride under conditions effective to form 4-chloro-3- nitro[1,5]naphthyridine; combining the mixture that includes the 4-chloro-3-nitro[1,5]naphthyridine with water under conditions effective to form solid 4-chloro-3-nitro[1,5]naphthyridine; separating at least a portion of the solid 4-chloro-3-nitro[1,5]naphthyridine from at least a portion of the mixture that includes the water; combining the separated solid 4-chloro-3-nitro[1,5]naphthyridine with a carrier that includes tetrahydrofuran; combining the 4-chloro-3-nitro[1,5]naphthyridine in the carrier with isobutylamine under conditions effective to form a mixture including $N^4$-(2-methylpropyl)-3-nitro[1,5]naphthyridin-4-amine; combining the mixture that includes the $N^4$-(2-methylpropyl)-3-nitro[1,5]naphthyridin-4-amine with water to form solid $N^4$-(2-methylpropyl)-3-nitro[1,5]naphthyridin-4-amine; and separating at least a portion of solid $N^4$-(2-methylpropyl)-3-nitro[1,5]naphthyridin-4-amine from at least a portion of the mixture that includes the water.

In one aspect, the invention provides a method for making 2-methyl-1-(2-methylpropyl)-5-oxido-1H-imidazo[4,5-c][1,5]naphthyridine. The method includes: providing $N^4$-(2-methylpropyl)-3-nitro[1,5]naphthyridin-4-amine in a carrier including toluene; combining the $N^4$-(2-methylpropyl)-3-nitro[1,5]naphthyridin-4-amine in the carrier with a hydrogenation catalyst and isopropanol to form a mixture; subjecting the mixture that includes the $N^4$-(2-methylpropyl)-3-nitro[1,5]naphthyridin-4-amine and the hydrogenation catalyst to a hydrogen atmosphere under conditions effective to form $N^4$-(2-methylpropyl)[1,5]naphthyridine-3,4-diamine; removing at least a portion of the hydrogenation catalyst from the $N^4$-(2-methylpropyl)[1,5]naphthyridine-3,4-diamine; removing at least a portion of the isopropanol from the mixture of $N^4$-(2-methylpropyl)[1,5]naphthyridine-3,4-diamine in a carrier that includes toluene and isopropanol; heating the $N^4$-(2-methylpropyl)[1,5]naphthyridine-3,4-diamine in the carrier to a temperature of 20° C. to 55° C.; combining the $N^4$-(2-methylpropyl)[1,5]naphthyridine-3,4-diamine in the carrier with p-toluenesulfonic acid to form a mixture; combining the mixture that includes the $N^4$-(2-methylpropyl)[1,5]naphthyridine-3,4-diamine and p-toluenesulfonic acid with a trialkyl orthoacetate at a temperature of 70° C. to 100° C.; maintaining the temperature at 70° C. to 100° C. for a period of time sufficient to form 2-methyl-1-(2-methylpropyl)-1H-imidazo[4,5-c][1,5]naphthyridine; cooling the mixture that includes 2-methyl-1-(2-methylpropyl)-1H-imidazo[4,5-c][1,5]naphthyridine to a temperature of 45° C. to 55° C.; combining the 2-methyl-1-(2-methylpropyl)-1H-imidazo[4,5-c][1,5]naphthyridine in the carrier with an oxidizing agent including peracetic acid to form a mixture; maintaining the mixture that includes the 2-methyl-1-(2-methylpropyl)-1H-imidazo[4,5-c][1,5]naphthyridine and peracetic acid at a temperature of 45° C. to 55° C. for a time sufficient to form 2-methyl-1-(2-methylpropyl)-5-oxido-1H-imidazo[4,5-c][1,5]naphthyridine; and isolating at least a portion of the 2-methyl-1-(2-methylpropyl)-5-oxido-1H-imidazo[4,5-c][1,5]naphthyridine.

In a preferred embodiment, providing $N^4$-(2-methylpropyl)-3-nitro[1,5]naphthyridin-4-amine (referred to above) includes: providing 3-nitro[1,5]naphthyridin-4-ol in a carrier including N,N-dimethylformamide; combining the 3-nitro[1,5]naphthyridin-4-ol in the carrier with phosphorous oxychloride under conditions effective to form 4-chloro-3-nitro[1,5]naphthyridine; combining the mixture that includes the 4-chloro-3-nitro[1,5]naphthyridine with water under conditions effective to form solid 4-chloro-3-nitro[1,5]naphthyridine; separating at least a portion of the solid 4-chloro-3-nitro[1,5]naphthyridine from at least a portion of the mixture that includes the water; combining the separated solid 4-chloro-3-nitro[1,5]naphthyridine with a carrier including tetrahydrofuran; combining the 4-chloro-3-nitro[1,5]naphthyridine in the carrier with isobutylamine under conditions effective to form a mixture that includes $N^4$-(2-methylpropyl)-3-nitro[1,5]naphthyridin-4-amine; combining the mixture that includes the $N^4$-(2-methylpropyl)-3-nitro[1,5]naphthyridin-4-amine with water to form solid $N^4$-(2-methylpropyl)-3-nitro[1,5]naphthyridin-4-amine; and separating at least a portion of solid $N^4$-(2-methylpropyl)-3-nitro[1,5]naphthyridin-4-amine from at least a portion of the mixture that includes the water.

The terms "comprising" and variations thereof do not have a limiting meaning where these terms appear in the description and claims.

As used herein, "a", "an", "the", "at least one", "at least a portion of" and "one or more" are used interchangeably.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the terms "alkyl" and the prefix "alk-" are inclusive of both straight chain and branched chain groups and of cyclic groups. Unless otherwise specified, these groups contain from 1 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, and cyclohexyl.

The term "aryl" in reference to "arylsulfonyl halide" includes carbocyclic aromatic rings or ring systems that may be unsubstituted or substituted. Examples of aryl groups include phenyl, naphthyl, biphenyl, fluorenyl and indenyl. Examples of substituents that may be present on the aryl group include alkyl, alkoxy, haloalkyl, haloalkoxy, halogen, nitro, hydroxy, cyano, aryl, aryloxy, and arylalkyleneoxy.

A "lower alcohol" (i.e., a $C_{1-4}$ alcohol) is understood to be a straight chain or branched chain alcohol containing one to four carbon atoms. Examples include, methanol, ethanol, n-propanol, isopropanol, n-butanol, sec-butanol, and tert-butanol.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS

2-Methyl-1-(2-methylpropyl)-1H-imidazo[4,5-c][1,5]naphthyridin-4-amine can be prepared according to the route shown in Scheme I. Each of these "steps" refers to a series of reactions and conditions described in greater detail below, and specifically as described in the EXAMPLES below.

It should be understood that each of these steps may be independently carried out with various of the other steps described herein and/or with various other methods not specifically described herein, such as, for example, in U.S. Pat.

No. 6,194,425 (Gerster, et al.). For example, steps (1) and (2) can be carried out as discussed herein, and various other methods can be used to convert the product of step 2 ($N^4$-(2-methylpropyl)-3-nitro[1,5]naphthyridin-4-amine) into the product of step 5 (2-methyl-1-(2-methylpropyl)-5-oxido-1H-imidazo[4,5-c][1,5]naphthyridine), which can then be used in the process of step (6) as described herein. Any one of steps (1) through (5) can also be carried out according to the methods described in U.S. Pat. No. 6,194,425 (Gerster, et al.).

This method then involves forming solid (i.e., precipitating) 4-chloro-3-nitro[1,5]naphthyridine using water. Typically, the mixture that includes the 4-chloro-3-nitro[1,5]naphthyridine is added to the water. In some embodiments, the conditions that allow for the formation of the solid include cooling the mixture that includes the water to a temperature of less than 20° C. In certain embodiments, the temperature is less than 15° C. Generally, the water is pre-cooled, and during Scheme I

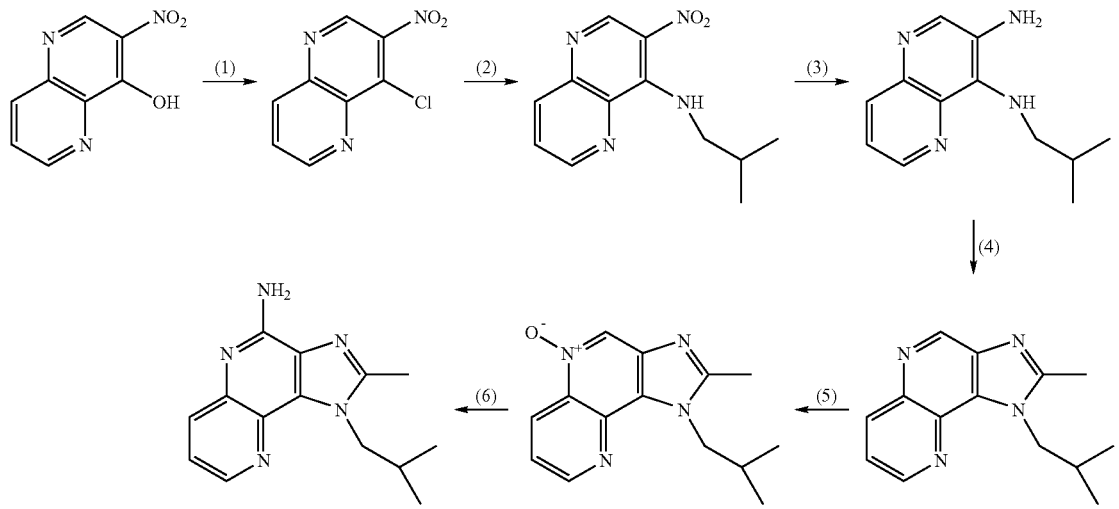

Referring to Scheme 1 (step 1), the present invention provides a method for preparing 4-chloro-3-nitro[1,5]naphthyridine. In some embodiments, the method includes: providing 3-nitro[1,5]naphthyridin-4-ol in a carrier that includes N,N-dimethylformamide (DMF); combining the 3-nitro[1,5]naphthyridin-4-ol in the carrier with phosphorous oxychloride under conditions effective to form 4-chloro-3-nitro[1,5]naphthyridine; combining the mixture that includes the 4-chloro-3-nitro[1,5]naphthyridine with water under conditions effective to form solid 4-chloro-3-nitro[1,5]naphthyridine; and separating at least a portion of the solid 4-chloro-3-nitro[1,5]naphthyridine from at least a portion of the mixture that includes the water.

Generally, this method is carried out under nitrogen, although other inert gases can be used (e.g., argon) if desired.

In this method, the DMF not only functions as a reaction solvent, but it typically reacts first with phosphorus oxychloride to form an active intermediate.

In some embodiments, combining the 3-nitro[1,5]naphthyridin-4-ol with phosphorous oxychloride involves using at least one equivalent of phosphorous oxychloride. Generally, the phosphorous oxychloride is added to the 3-nitro-[1,5]naphthyridin-4-ol. Preferably, this addition occurs relatively slowly (e.g., over a period of at least 30 minutes).

In some embodiments, the conditions effective to form 4-chloro-3-nitro[1,5]naphthyridine include a temperature of at least 15° C. In some embodiments, the temperature is at least 20° C. In some embodiments, the conditions effective to form 4-chloro-3-nitro[1,5]naphthyridine include a temperature of no greater than 35° C. In some embodiments, the temperature is no greater than 20° C. In some embodiments, these conditions include a time period of at least one hour, and, if desired, up to 21 hours.

the addition, the mixture is maintained at a temperature of less than 20° C. In certain embodiments, the temperature is at least 5° C.

In some embodiments, separating at least a portion of the solid 4-chloro-3-nitro[1,5]naphthyridine involves filtering the solid 4-chloro-3-nitro[1,5]naphthyridine from the mixture that includes the water. One skilled in the art will appreciate, however, that there are many other ways to separate the solid (i.e., a precipitate) from the mixture, such as decanting and centrifugation. After separation, the precipitate may optionally be washed with water to remove impurities.

In some embodiments, separating at least a portion of the solid 4-chloro-3-nitro[1,5]naphthyridine occurs less than 30 minutes after combining the mixture that includes the 4-chloro-3-nitro[1,5]naphthyridine with water.

In some embodiments, the solid 4-chloro-3-nitro[1,5]naphthyridine is used in the next step (step 2 of Scheme 1, e.g., combined with isobutylamine, as discussed in greater detail below) within less than 4 hours of its preparation.

Referring to Scheme 1 (step 2), the present invention provides a method for preparing $N^4$-(2-methylpropyl)-3-nitro[1,5]naphthyridin-4-amine. This method includes: providing 4-chloro-3-nitro[1,5]naphthyridine in a carrier that includes a water-miscible organic liquid; combining the 4-chloro-3-nitro[1,5]naphthyridine in the carrier with isobutylamine under conditions effective to form a mixture including $N^4$-(2-methylpropyl)-3-nitro[1,5]naphthyridin-4-amine; combining the mixture that includes the $N^4$-(2-methylpropyl)-3-nitro[1,5]naphthyridin-4-amine with water; and separating at least a portion of solid $N^4$-(2-methylpropyl)-3-nitro[1,5]naphthyridin-4-amine from at least a portion of the mixture that includes the water.

In some embodiments, the water-miscible organic liquid is selected from the group consisting of tetrahydrofuran, dichloromethane, acetonitrile, and mixtures thereof. In some embodiments, the water-miscible organic liquid is tetrahydrofuran.

In some embodiments, the 4-chloro-3-nitro[1,5]naphthyridine is combined with at least two equivalents of isobutylamine. This provides one equivalent used to scavenge the HCl formed during the reaction and another one to react with 4-chloro-3-nitro[1,5]naphthyridine. In some embodiments, at least 2.05 equivalents are used, and in some embodiments up to 2.4 equivalents are used if desired.

Generally, the isobutylamine is added to the 4-chloro-3-nitro[1,5]naphthyridine in the water-miscible organic liquid. This addition preferably occurs relatively slowly (e.g., over a period of at least 30 minutes).

In some embodiments, the conditions effective to form $N^4$-(2-methylpropyl)-3-nitro[1,5]naphthyridin-4-amine include a temperature of at least 15° C. In some embodiments, the temperature is at least 20° C. In some embodiments, the temperature is at most 30° C. In some embodiments, this temperature is maintained for at least 30 minutes, and in some embodiments for at least 3 hours.

Water is then typically used to precipitate solid $N^4$-(2-methylpropyl)-3-nitro[1,5]naphthyridin-4-amine, although solid $N^4$-(2-methylpropyl)-3-nitro[1,5]naphthyridin-4-amine can form before the reaction mixture is added to water or water is added to the reaction mixture.

In some embodiments, separating at least a portion of the solid $N^4$-(2-methylpropyl)-3-nitro[1,5]naphthyridin-4-amine involves filtering the solid $N^4$-(2-methylpropyl)-3-nitro[1,5]naphthyridin-4-amine. One skilled in the art will appreciate, however, that there are many other ways to separate the solid (i.e., a precipitate) from the mixture, such as decanting and centrifugation.

The method can further include washing and drying this solid if desired. For example, after separation, the precipitate may optionally be washed with water to remove impurities. One skilled in the art will appreciate that there are many ways to dry the precipitate. This includes, for example, using elevated temperatures, desiccation, reduced pressure, using a dry (e.g., nitrogen) atmosphere, and the like. In one embodiment, drying the precipitate occurs at a temperature range of 45° C. to 55° C. while under at least a partial vacuum. In another method, at least partially drying the precipitate occurs under at least a partial vacuum.

Referring to Scheme 1 (step 3), the present invention provides a method for preparing $N^4$-(2-methylpropyl)[1,5]naphthyridine-3,4-diamine. This method involves: providing $N^4$-(2-methylpropyl)-3-nitro[1,5]naphthyridin-4-amine in a carrier that includes a non-chlorinated solvent; combining the $N^4$-(2-methylpropyl)-3-nitro[1,5]naphthyridin-4-amine in the carrier with a hydrogenation catalyst to form a mixture; subjecting the mixture that includes the $N^4$-(2-methylpropyl)-3-nitro[1,5]naphthyridin-4-amine and the hydrogenation catalyst to a hydrogen atmosphere under conditions effective to form $N^4$-(2-methylpropyl)[1,5]naphthyridine-3,4-diamine; and removing at least a portion of the hydrogenation catalyst from the $N^4$-(2-methylpropyl)[1,5]naphthyridine-3,4-diamine.

In some embodiments, the non-chlorinated solvent is selected from the group consisting of toluene, butyl acetate, ethyl acetate, and combinations thereof. In some embodiments, the non-chlorinated solvent is toluene.

In some embodiments, combining the $N^4$-(2-methylpropyl)-3-nitro[1,5]naphthyridin-4-amine in the carrier with a hydrogenation catalyst includes combining the $N^4$-(2-methylpropyl)-3-nitro[1,5]naphthyridin-4-amine in the carrier with a hydrogenation catalyst and isopropanol to form a mixture. The hydrogenation catalyst and isopropanol can be added simultaneously or sequentially in either order.

In some embodiments, the hydrogenation catalyst includes platinum, although it is believed that palladium may also work. Preferably the hydrogenation catalyst is platinum on carbon. A preferred load level of platinum on carbon is at least 1.5 weight percent of platinum metal on carbon. Typical load levels of platinum on carbon at up to 10 weight percent of platinum metal on carbon.

In some embodiments, the conditions effective to form $N^4$-(2-methylpropyl)[1,5]naphthyridine-3,4-diamine include a temperature of at least 15° C. In some embodiments, this temperature is at least 18° C. In some embodiments, the conditions effective to form $N^4$-(2-methylpropyl)[1,5]naphthyridine-3,4-diamine include a temperature of no greater than 30° C. In some embodiments, this temperature is no greater than 25° C.

In some embodiments, the conditions effective to form $N^4$-(2-methylpropyl)[1,5]naphthyridine-3,4-diamine include a hydrogen pressure of $1 \times 10^5$ Pa to $3 \times 10^5$ Pa (i.e., 1 bar to 3 bars), although higher pressures can be used. It is desirable to use the lowest hydrogen pressure possible to avoid equipment concerns.

In some embodiments, the conditions effective to form $N^4$-(2-methylpropyl)[1,5]naphthyridine-3,4-diamine include a time period of at least 3 hours. Shorter reaction times may be possible, however, this can depend on the hydrogenation vessel (stirrer) and on the operating conditions (e.g., dilution, quantity of catalyst). Longer reaction times (e.g., up to 22 hours) are also possible.

In some embodiments, the method involves subsequently removing at least a portion of the isopropanol from the mixture of $N^4$-(2-methylpropyl)[1,5]naphthyridine-3,4-diamine in a carrier that includes toluene and isopropanol.

Generally, the hydrogenation catalyst is removed and, in some embodiments, the $N^4$-(2-methylpropyl)[1,5]naphthyridine-3,4-diamine is used in the next step (step 4 of Scheme 1, e.g., combined with an organic acid, as discussed in greater detail below) without being isolated.

Referring to Scheme 1 (step 4), the present invention provides a method for preparing 2-methyl-1-(2-methylpropyl)-1H-imidazo[4,5-c][1,5]naphthyridine. The method includes: providing $N^4$-(2-methylpropyl)[1,5]naphthyridine-3,4-diamine in a carrier including a non-chlorinated solvent at a temperature of at least 18° C. (and typically no more than 30° C.); combining the $N^4$-(2-methylpropyl)[1,5]naphthyridine-3,4-diamine in the carrier with an organic acid to form a mixture; combining the mixture that includes the $N^4$-(2-methylpropyl)[1,5]naphthyridine-3,4-diamine and organic acid with a trialkyl orthoacetate at a temperature of at least 70° C. (and typically no more than 100° C., and preferably no more than 90° C.); and maintaining the temperature at least 70° C. (and typically no more than 100° C.) for a sufficient time to form 2-methyl-1-(2-methylpropyl)-1H-imidazo[4,5-c][1,5]naphthyridine.

In some embodiments, the non-chlorinated solvent is selected from the group consisting of toluene, butyl acetate, ethyl acetate, and combinations thereof. In some embodiments, the non-chlorinated solvent is toluene.

In some embodiments, the organic acid is selected from the group consisting of p-toluenesulfonic acid, trifluoroacetic acid, ethanesulfonic acid, and mixtures thereof. In some embodiments, the organic acid is p-toluenesulfonic acid.

In some embodiments, at least 0.02 equivalent of an organic acid is used. In some embodiments, up to 0.08 equivalent of an organic acid is used.

Generally, the organic acid is added to the $N^4$-(2-methylpropyl)[1,5]naphthyridine-3,4-diamine in a carrier including a non-chlorinated solvent (e.g., the material from step (3) of Scheme I).

In some embodiments, the trialkyl orthoacetate can be triethyl orthoacetate or trimethyl orthoacetate. In some embodiments, the trialkyl orthoacetate is triethyl orthoacetate.

In some embodiments, at least one equivalent of the trialkyl orthoacetate is used. In some embodiments, at least 1.1 equivalents of a trialkyl orthoacetate are used. In some embodiments, up to 1.4 equivalents of a trialkyl orthoacetate are used.

In some embodiments, combining the mixture that includes the $N^4$-(2-methylpropyl)[1,5]naphthyridine-3,4-diamine and organic acid with a trialkyl orthoacetate occurs by heating the mixture of $N^4$-(2-methylpropyl)[1,5]naphthyridine-3,4-diamine and organic acid to a temperature of 70° C. to 100° C., followed by adding the trialkyl orthoacetate to the mixture. Generally, this addition occurs relatively slowly (e.g., over a period of at least 30 minutes).

In some embodiments, maintaining the temperature at 70° C. to 100° C. for a period time sufficient to form 2-methyl-1-(2-methylpropyl)-1H-imidazo[4,5-c][1,5]naphthyridine involves maintaining the temperature at 70° C. to 100° C. for at least 30 minutes. In some embodiments, the temperature is maintained at 70° C. to 100° C. for at least 2 hours. In some embodiments, the temperature is maintained at 70° C. to 100° C. for up to 6 hours.

In some embodiments, the method further includes a step of cooling the mixture that includes 2-methyl-1-(2-methylpropyl)-1H-imidazo[4,5-c][1,5]naphthyridine to a temperature of no greater than 70° C., preferably no greater than 55° C. Typically, this temperature is at least 25° C., preferably at least 40° C., and more preferably at least 45° C.

In some embodiments, the 2-methyl-1-(2-methylpropyl)-1H-imidazo[4,5-c][1,5]naphthyridine is used in the next step of the process (step 5 of Scheme I, e.g., and combined with an oxidizing agent) without being isolated.

Referring to Scheme 1 (step 5), the present invention provides a method for preparing 2-methyl-1-(2-methylpropyl)-5-oxido-1H-imidazo[4,5-c][1,5]naphthyridine. This method includes: providing 2-methyl-1-(2-methylpropyl)-1H-imidazo[4,5-c][1,5]naphthyridine in a carrier that includes a non-chlorinated solvent at a temperature of at least 25° C. (and typically up to 70° C.); combining the 2-methyl-1-(2-methylpropyl)-1H-imidazo[4,5-c][1,5]naphthyridine in the carrier with an oxidizing agent to form a mixture and maintaining the mixture at a temperature of at least 25° C. (and typically up to 70° C.) for a period of time sufficient to form 2-methyl-1-(2-methylpropyl)-5-oxido-1H-imidazo[4,5-c][1,5]naphthyridine; and isolating at least a portion of the 2-methyl-1-(2-methylpropyl)-5-oxido-1H-imidazo[4,5-c][1,5]naphthyridine.

In some embodiments, the non-chlorinated solvent is selected from the group consisting of toluene, butyl acetate, ethyl acetate, and combinations thereof. In some embodiments, the non-chlorinated solvent is toluene.

In some embodiments, the temperature of the 2-methyl-1-(2-methylpropyl)-1H-imidazo[4,5-c][1,5]naphthyridine in a carrier that includes a non-chlorinated solvent is a temperature of at least 40° C., and in other embodiments, the temperature is at least 45° C. In some embodiments, the temperature of the 2-methyl-1-(2-methylpropyl)-1H-imidazo[4,5-c][1,5]naphthyridine in a carrier that includes a non-chlorinated solvent is a temperature of at most 55° C.

In some embodiments, the oxidizing agent includes peracetic acid, although other similar oxidizing agents could be used if desired. In some embodiments, at least one equivalent of oxidizing agent (preferably peracetic acid) is used. In some embodiments, at least 1.2 equivalents of oxidizing agent are used.

Generally, the oxidizing agent is added to the 2-methyl-1-(2-methylpropyl)-1H-imidazo[4,5-c][1,5]naphthyridine.

The oxidizing agent addition is generally exothermic. With peracetic acid, there is a theoretical adiabatic temperature rise of 29° C. if all the acid is added at once. Therefore, this addition is preferably carried out in a controlled manner to maintain the reaction mixture in the desired temperature range. Preferably, the addition is carried out over at least 2 hours. Preferably, subsequent stirring is carried out for a period of at least 4 hours.

In some embodiments, the mixture of 2-methyl-1-(2-methylpropyl)-1H-imidazo[4,5-c][1,5]naphthyridine in the carrier with an oxidizing agent is maintained at a temperature of at least 40° C. In some embodiments, the mixture of 2-methyl-1-(2-methylpropyl)-1H-imidazo[4,5-c][1,5]naphthyridine in the carrier with an oxidizing agent is maintained at a temperature of at least 45° C. In some embodiments, the mixture of 2-methyl-1-(2-methylpropyl)-1H-imidazo[4,5-c][1,5]naphthyridine in the carrier with an oxidizing agent is maintained at a temperature of at most 55° C.

In some embodiments, the period of time sufficient to form 2-methyl-1-(2-methylpropyl)-5-oxido-1H-imidazo[4,5-c][1,5]naphthyridine includes a period of time sufficient to react at least 80% of the 2-methyl-1-(2-methylpropyl)-1H-imidazo[4,5-c][1,5]naphthyridine. In some embodiments, the period of time sufficient to react at least 80% of the 2-methyl-1-(2-methylpropyl)-1H-imidazo[4,5-c][1,5]naphthyridine is at least 5 hours (and often up to 7 hours).

In some embodiments, isolating the 2-methyl-1-(2-methylpropyl)-5-oxido-1H-imidazo[4,5-c][1,5]naphthyridine includes: combining the mixture that includes the 2-methyl-1-(2-methylpropyl)-5-oxido-1H-imidazo[4,5-c][1,5]naphthyridine with an aqueous solution of a reducing agent followed by an aqueous base; cooling the mixture to form solid 2-methyl-1-(2-methylpropyl)-5-oxido-1H-imidazo[4,5-c][1,5]naphthyridine; and separating at least a portion of the solid 2-methyl-1-(2-methylpropyl)-5-oxido-1H-imidazo[4,5-c][1,5]naphthyridine from at least a portion of the mixture.

In some embodiments, the reducing agent is selected from the group consisting of sodium metabisulfite, sodium sulfite, ferrous sulfate, and combinations thereof. In some embodiments, the reducing agent is sodium metabisulfite.

In some embodiments, an aqueous solution of at least 0.1 equivalent sodium metabisulfite is used. In some embodiments, an aqueous solution of at least 0.3 equivalent sodium metabisulfite is used.

In some embodiments, a sufficient amount of aqueous base is used to adjust the mixture to a pH of greater than 10. Typically, 4 to 4.5 equivalents of sodium hydroxide are used to reach the targeted pH.

In some embodiments, six to ten milliliters of water per gram of 2-methyl-1-(2-methylpropyl)-5-oxido-1H-imidazo[4,5-c][1,5]naphthyridine are combined with a mixture of eight to twelve milliliters of toluene per gram of 2-methyl-1-(2-methylpropyl)-5-oxido-1H-imidazo[4,5-c][1,5]naphthyridine. Preferably, the volume ratio of water to toluene is 0.8:1.

In some embodiments, the cooling step involves cooling to a temperature of no greater than 20° C. In some embodiments, the cooling step involves cooling to a temperature of no greater than 7° C. In some embodiments, the cooling step involves cooling to a temperature of at least 0° C. In some embodiments, the cooling step involves cooling to a temperature of at least 3° C.

In some embodiments, separating at least a portion of the solid 2-methyl-1-(2-methylpropyl)-5-oxido-1H-imidazo[4,5-c][1,5]naphthyridine involves separating by centrifugation. One skilled in the art will appreciate, however, that there are many other ways to separate the solid (i.e., a precipitate) from the mixture, such as decanting and filtering.

Referring to Scheme 1 (step 6), the present invention provides a method for preparing 2-methyl-1-(2-methylpropyl)-1H-imidazo[4,5-c][1,5]naphthyridin-4-amine. The method includes providing 2-methyl-1-(2-methylpropyl)-5-oxido-1H-imidazo[4,5-c][1,5]naphthyridine in a carrier that includes a lower alcohol; combining the 2-methyl-1-(2-methylpropyl)-5-oxido-1H-imidazo[4,5-c][1,5]naphthyridine in the carrier with an ammonia- or ammonium-containing reagent and an arylsulfonyl halide to form a mixture; allowing the components of the mixture to react for a period of time sufficient to form 2-methyl-1-(2-methylpropyl)-1H-imidazo[4,5-c][1,5]naphthyridin-4-amine.

Generally, this method is carried out under nitrogen, although other inert gases can be used (e.g., argon) if desired.

In some embodiments, the step of providing 2-methyl-1-(2-methylpropyl)-5-oxido-1H-imidazo[4,5-c][1,5]naphthyridine in a carrier that includes a lower alcohol occurs at a temperature of at least 20° C. In some embodiments, this temperature is no greater than 30° C.

In some embodiments of this method, the ammonia- or ammonium-containing reagent is preferably added prior to the arylsulfonyl halide.

In some embodiments of this method, the ammonia- or ammonium-containing reagent includes ammonium hydroxide in water. In some embodiments, the ammonia- or ammonium-containing reagent includes less than ten equivalents of ammonium hydroxide.

In some embodiments, combining the 2-methyl-1-(2-methylpropyl)-5-oxido-1H-imidazo[4,5-c][1,5]naphthyridine in the carrier with an ammonia- or ammonium-containing reagent is carried out at a temperature of at least 20° C. In some embodiments, this temperature is no greater than 30° C.

In some embodiments, the ammonia- or ammonium-containing reagent is added to the 2-methyl-1-(2-methylpropyl)-5-oxido-1H-imidazo[4,5-c][1,5]naphthyridine. This addition preferably occurs relatively quickly with continuous agitation. One skilled in the art will appreciate that there are many means for agitating a mixture such as stirring, shaking, and sonicating.

In some embodiments, the arylsulfonyl halide is benzenesulfonyl chloride or p-toluenesulfonyl chloride.

In some embodiments, combining an arylsulfonyl halide (typically after the ammonia- or ammonium-containing compound is added) is carried out at a temperature of at least 20° C. In some embodiments, this temperature is no greater than 30° C.

In some embodiments, allowing the components of the mixture to react for a period of time sufficient to form 2-methyl-1-(2-methylpropyl)-1H-imidazo[4,5-c][1,5]naphthyridin-4-amine is carried out at a temperature of at least 20° C. In some embodiments, this temperature is no greater than 30° C.

In some embodiments, the period of time sufficient to form 2-methyl-1-(2-methylpropyl)-1H-imidazo[4,5-c][1,5]naphthyridin-4-amine is at least 45 minutes. In some embodiments, this period of time is no greater than 75 minutes.

In some embodiments, the method further includes a step of combining the mixture with an aqueous base. Typically, sufficient aqueous base is added to adjust the mixture to a pH of greater than 8, and preferably greater than 10.

In some embodiments of this method, the aqueous base is aqueous sodium hydroxide, although other alkali metal hydroxides (e.g., potassium hydroxide) or other aqueous bases (e.g., sodium carbonate, potassium carbonate) could be used if desired.

In some embodiments, the method further includes a step of cooling the mixture to a temperature of no greater than 15° C. In some embodiments, this temperature is at least 15° C.

In some embodiments this method can further include separating at least a portion of the resultant 2-methyl-1-(2-methylpropyl)-1H-imidazo[4,5-c][1,5]naphthyridin-4-amine from at least a portion of the mixture, and, if desired, further include washing and at least partially drying the resultant 2-methyl-1-(2-methylpropyl)-1H-imidazo[4,5-c][1,5]naphthyridin-4-amine.

One skilled in the art will appreciate that there are many ways to separate a precipitate from the mixture, such as filtering, decanting, and centrifugation. After separation, the precipitate may optionally be washed with water to remove impurities. Furthermore, one skilled in the art will appreciate that there are many ways to at least partially dry the precipitate. This includes, for example, using elevated temperatures, desiccation, reduced pressure, using a dry (e.g., nitrogen) atmosphere, and the like. In one embodiment, at least partially drying the precipitate occurs at a temperature range of 25° C. to 60° C. under at least a partial vacuum.

EXAMPLES

Objects and advantages of this invention are further illustrated by the following examples, but the particular materials and amounts thereof recited in these examples, as well as other conditions and details, should not be construed to unduly limit this invention.

Example 1

Preparation of $N^4$-(2-Methylpropyl)-3-nitro[1,5]naphthyridin-4-amine

Part A

Under a nitrogen atmosphere, a suspension of 3-nitro[1,5]naphthyridin-4-ol (12.00 kg, 67.78 mol) in DMF (49 L) was stirred for 30 minutes at a temperature of 20° C. to 24° C. Phosphorous oxychloride (10.6 kg, 69.1 mol) was added slowly over a period of 53 minutes while maintaining the temperature at 20.6° C. to 25.6° C. Additional DMF (5 L) was used to rinse the addition vessel and added to the reaction. The reaction was stirred for 19 hours and 17 minutes at a temperature of 20° C. to 24° C. and then added quickly, over a period of four minutes, to purified water (275 L) that had been cooled to 8.4° C. During the addition, the temperature of the mixture did not exceed 18° C. Additional water (80 L) was used to rinse the original vessel and added quickly to the resulting mixture, which ranged in temperature from 16.6° C. to 17.2° C. during this addition. The mixture resulting from the additions was stirred for 30 minutes while cooling to a temperature of approximately 10° C. A solid formed and was isolated by filtration and washed with cold water (6×33 L at 10° C.) to provide 20.55 kg of 4-chloro-3-nitro[1,5]naphthyridine, which contained some water and was used in Part B within 2.75 hours of filtration.

Part B

Isobutylamine (9.4 kg, 12.8 L, 130 mol) was added to a stirred suspension of the material from Part A (20.55 kg) in tetrahydrofuran (67 L) over a period of 77 minutes while maintaining a reaction temperature of 20° C. to 27° C. The addition of isobutylamine was followed by a rinse with tetrahydrofuran (5 L). The reaction was stirred for 190 minutes at a temperature of 20° C. to 24° C., and then water (288 L) was added over a period of about one hour while maintaining the reaction temperature at 21.4° C. to 23.8° C. The resulting mixture was stirred at 20° C. to 24° C. for 75 minutes and then filtered. The isolated solid was washed with water (4×25 L) that had also been used to rinse the reaction vessel, pulled dry under vacuum, and further dried under vacuum for 60 hours at a temperature of 45° C. to 55° C. to provide 13.7 kg of $N^4$-(2-methylpropyl)-3-nitro[1,5]naphthyridin-4-amine.

Example 2

Preparation of $N^4$-(2-Methylpropyl)-3-nitro[1,5]naphthyridin-4-amine

Part A

Under a nitrogen atmosphere, a suspension of 3-nitro[1,5]naphthyridin-4-ol (1.00 kg, 5.23 mol) in DMF (4.5 L) was cooled in an ice bath. Phosphorous oxychloride (882.5 g, 5.75 mol) was added slowly over a period of one hour while maintaining the temperature at 16° C. to 20° C. After the addition was complete, the reaction was stirred for three hours at a temperature of 20° C. to 24° C. and then added quickly to two portions of demineralized water (12.5 L each) at 20° C. to 24° C. During the addition, the temperature of the mixtures was allowed to reach 29.5° C. to 30.5° C. The resulting mixtures were cooled to a temperature of approximately 10° C. over a period of 60 minutes. A solid formed in each mixture and was isolated by filtration, and each solid was washed with demineralized water (2×2 L and 1×1 L) until the pH of the filtrate equaled the pH of demineralized water. The tan solid product, 4-chloro-3-nitro[1,5]naphthyridine, contained water and was used in Part B within one hour.

Part B

Isobutylamine (784 g, 10.7 mol) was added to a suspension of the material from Part A in tetrahydrofuran (6 L) over a period of 45 minutes while maintaining a reaction temperature of 17° C. to 27° C. When the addition was 75% complete, yellow needles formed in the solution. After the addition was complete, the reaction was stirred for 30 minutes at a temperature of 21.5° C. to 22.5° C. and then added with stirring to two portions of demineralized water (12 L each). The resulting mixtures were stirred for 30 minutes. The solid formed in each mixture was isolated by filtration, and each solid was washed with demineralized water (2×2 L) until the pH of the filtrate equaled the pH of demineralized water. The solids were then dried overnight on the filter funnels to provide 1.225 kg of $N^4$-(2-methylpropyl)-3-nitro[1,5]naphthyridin-4-amine as a yellow solid.

Example 3

Preparation of 2-Methyl-1-(2-methylpropyl)-1H-imidazo[4,5-c][1,5]naphthyridin-5-oxide Part A A hydrogenation vessel was charged with $N^4$-(2-methylpropyl)-3-nitro[1,5]naphthyridin-4-amine (7.50 kg, 30.5 mol) and toluene (125.0 kg). A suspension of 3% platinum on carbon (0.44 kg, approximately 33% by weight (w/w) in water) in isopropanol (7.0 kg) was added to the vessel followed by a rinse with toluene (10.0 kg). The reaction mixture was then placed under hydrogen pressure ($2.4 \times 10^5$ Pa, 2.4 bars) for six hours while stirring and maintaining the temperature at 22° C. The reaction mixture was then filtered, and the filter cake was washed with toluene (30.0 kg). The filtrate was concentrated under reduced pressure ($1 \times 10^4$ Pa, 0.1 bar) at approximately 50° C. to provide a solution of $N^4$-(2-methylpropyl)[1,5]naphthyridine-3,4-diamine in toluene (75 L, approximately 10 mL/g).

Part B

The solution from Part A (75 L) was heated to a temperature of 50° C., and p-toluenesulfonic acid monohydrate (0.35 kg, 1.8 mol) was added. The reaction was heated to a temperature of 80° C., and triethyl orthoacetate (5.70 kg, 35.1 mol) was slowly added with stirring over a period of 40 minutes. The reaction was stirred at 80° C. for two hours and then cooled to 50° C. to provide a solution of 2-methyl-1-(2-methylpropyl)-1H-imidazo[4,5-c][1,5]naphthyridine in toluene.

Part C

Peracetic acid (7.15 kg of 40% w/w) was added over a period of 60 minutes to the 50° C. solution from Part B. The reaction was stirred for six hours at 50° C., and then cooled to 5° C. Aqueous sodium metabisulfite (46.2 kg of 2.5% w/w), and aqueous sodium hydroxide (19.50 kg of 25% w/w, to achieve pH 13) were carefully added sequentially. The resulting suspension was stirred at 5° C. for one hour and then separated by centrifugation. A solid was collected and dried under vacuum ($2 \times 10^3$ Pa, 0.02 bar) at 30° C. for 24 hours to provide 2-methyl-1-(2-methylpropyl)-1H-imidazo[4,5-c][1,5]naphthyridin-5-oxide as a yellow solid.

Example 4

Preparation of 2-Methyl-1-(2-methylpropyl)-1H-imidazo[4,5-c][1,5]naphthyridin-4-amine Under a nitrogen atmosphere, aqueous ammonium hydroxide (four equivalents) was quickly added with continuous stirring to a suspension of 2-methyl-1-(2-methylpropyl)-1H-imidazo[4,5-c][1,5]naphthyridin-5-oxide in methanol (6 mL/g) while maintaining the reaction temperature at 20° C. to 24° C. Methanol was used to rinse the addition vessel and added to the reaction. The reaction was stirred until all material was dissolved. With continuous stirring, benzenesulfonyl chloride (2 equivalents) was added over a period of 15 to 45 minutes while maintaining the reaction temperature at 20° C. to 30° C. Methanol was used to rinse the addition vessel and added to the reaction. The reaction was stirred for 45 to 75 minutes at 20° C. to 24° C. Aqueous sodium hydroxide (3 equivalents of 10% w/w) was added to the reaction mixture over a period of 15 to 45 minutes while maintaining the reaction temperature between 20° C. and 25° C. Water (10 L), used to rinse the addition vessel, was added to the reaction mixture. The resulting mixture was cooled to 10° C. and stirred for 2 to 24 hours. A precipitate was present and was isolated by filtration and washed with deionized water until the filtrate was pH 7. The solid was dried at 50° C. under vacuum to provide 2-methyl-1-(2-methylpropyl)-1H-imidazo[4,5-c][1,5]naphthyridin-4-amine as an off-white solid.

Example 5

Preparation of 2-Methyl-1-(2-methylpropyl)-1H-imidazo[4,5-c][1,5]naphthyridin-4-amine Aqueous ammonium hydroxide (5.07 kg of 30% w/w) was added over a period of ten minutes to a suspension of 2-methyl-1-(2-methylpropyl)-1H-imidazo[4,5-c][1,5]naphthyridin-5-oxide (6.00 kg, 23.4 mol) in ethanol (23.2 kg) at 22° C. The reaction was stirred for five minutes. Benzenesulfonyl chloride (8.80 kg, 49.8 mol) was added over a period of 30 minutes. The reaction was stirred for one hour at 22° C. A solution of aqueous sodium hydroxide (15.0 kg of 25% w/w) and water (34.0 kg) was added to the reaction mixture over a period of 30 minutes at 22° C. to adjust the mixture to pH 13. The resulting mixture was cooled to 11° C. and stirred at that temperature for three hours and then separated by centrifugation. A solid was collected, washed with demineralized water (105.0 kg) at 22° C. until the filtrate was pH 7, and dried under vacuum ($2 \times 10^3$ Pa, 0.02 bar) at 45° C. for 24 hours to provide 2-methyl-1-(2-methylpropyl)-1H-imidazo[4,5-c][1,5]naphthyridin-4-amine.

What is claimed is:

1. A method for preparing 2-methyl-1-(2-methylpropyl)-1H-imidazo[4,5-c][1,5]naphthyridin-4-amine, the method comprising:
    providing 2-methyl-1-(2-methylpropyl)-5-oxido-1H-imidazo[4,5-c][1,5]naphthyridine in a carrier comprising a lower alcohol;
    combining the 2-methyl-1-(2-methylpropyl)-5-oxido-1H-imidazo[4,5-c][1,5]naphthyridine in the carrier with an ammonia- or ammonium-containing reagent and an arylsulfonyl halide to form a mixture; and
    allowing the components of the mixture to react for a period of time sufficient to form 2-methyl-1-(2-methylpropyl)-1H-imidazo[4,5-c][1,5]naphthyridin-4-amine.

2. The method of claim 1 further comprising combining the mixture with an aqueous base.

3. The method of claim 2 wherein sufficient aqueous base is added to adjust the mixture to a pH of greater than 8.

4. The method of claim 3 wherein the aqueous base comprises aqueous sodium hydroxide.

5. The method of claim 1 wherein the ammonia- or ammonium-containing reagent comprises ammonium hydroxide in water.

6. The method of claim 5 wherein the ammonia- or ammonium-containing reagent comprises less than ten equivalents of ammonium hydroxide.

7. The method of claim 1 wherein the arylsulfonyl halide is benzenesulfonyl chloride or p-toluenesulfonyl chloride.

8. The method of claim 1 wherein the period of time sufficient to form 2-methyl-1-(2-methylpropyl)-1H imidazo[4,5-c][1,5]naphthyridin-4-amine is 45 minutes to 75 minutes.

9. The method of claim 1 wherein providing 2-methyl-1-(2-methylpropyl)-5-oxido-1H-imidazo[4,5-c][1,5]naphthyridine in a carrier comprising a lower alcohol; combining the 2-methyl-1-(2-methylpropyl)-5-oxido-1H-imidazo[4,5-c][1,5]naphthyridine in the carrier with an ammonia- or ammonium-containing reagent and an arylsulfonyl halide to form a mixture; and allowing the components of the mixture to react for a period of time sufficient to form 2-methyl-1-(2-methylpropyl)-1H-imidazo[4,5-c][1,5]naphthyridin-4-amine are carried out at a temperature of 20° C. to 30° C.

10. The method of claim 1 wherein the ammonia- or ammonium-containing reagent is added prior to the arylsulfonyl halide.

11. The method of claim 1 further comprising cooling the mixture to a temperature of 5° C. to 15° C.

12. The method of claim 1 further comprising separating at least a portion of the 2-methyl-1-(2-methylpropyl)-1H-imidazo[4,5-c][1,5]naphthyridin-4-amine from at least a portion of the mixture.

13. The method of claim 12 further comprising washing and at least partially drying the 2-methyl-1-(2-methylpropyl)-1H-imidazo[4,5-c][1,5]naphthyridin-4-amine.

14. The method of claim 1 wherein providing 2-methyl-1-(2-methylpropyl)-5-oxido-1H-imidazo[4,5-c][1,5]naphthyridine comprises:
    providing 2-methyl-1-(2-methylpropyl)-1H-imidazo[4,5-c][1,5]naphthyridine in a carrier comprising a non-chlorinated solvent at a temperature of 25° C. to 70° C.;
    combining the 2-methyl-1-(2-methylpropyl)-1H-imidazo[4,5-c][1,5]naphthyridine in the carrier with an oxidizing agent to form a mixture and maintaining the mixture at a temperature of 25° C. to 70° C. for a period of time sufficient to form 2-methyl-1-(2-methylpropyl)-5-oxido-1H-imidazo[4,5-c][1,5]naphthyridine; and
    isolating at least a portion of the 2-methyl-1-(2-methylpropyl)-5-oxido-1H-imidazo[4,5-c][1,5]naphthyridine.

15. The method of claim 14 wherein the non-chlorinated solvent is selected from the group consisting of toluene, butyl acetate, ethyl acetate, and combinations thereof.

16. The method of claim 15 wherein the non-chlorinated solvent is toluene.

17. The method of claim 14 wherein the oxidizing agent comprises peracetic acid.

18. The method of claim 14 wherein the period of time sufficient to form 2-methyl-1-(2-methylpropyl)-5-oxido-1H-imidazo[4,5-c][1,5]naphthyridine comprises a period of time sufficient to react at least 80% of the 2-methyl-1-(2-methylpropyl)-1H-imidazo[4,5-c][1,5]naphthyridine.

19. The method of claim 18 wherein the period of time sufficient to react at least 80% of the 2-methyl-1-(2-methylpropyl)-1H-imidazo[4,5-c][1,5]naphthyridine is 5 hours to 7 hours.

20. The method of claim 14 wherein isolating the 2-methyl-1-(2-methylpropyl)-5-oxido-1H-imidazo[4,5-c][1,5]naphthyridine comprises:
    combining the mixture comprising the 2-methyl-1-(2-methylpropyl)-5-oxido-1H-imidazo[4,5-c][1,5]naphthyridine with an aqueous solution of a reducing agent followed by an aqueous base;
    cooling the mixture to form solid 2-methyl-1-(2-methylpropyl)-5-oxido-1H-imidazo[4,5-c][1,5]naphthyridine; and
    separating at least a portion of the solid 2-methyl-1-(2-methylpropyl-5-oxido-1H-imidazo[4,5-c][1,5]naphthyridine from at least a portion of the mixture.

21. The method of claim 20 wherein the reducing agent is selected from the group consisting of sodium metabisulfite, sodium sulfite, ferrous sulfate, and combinations thereof.

22. The method of claim 21 wherein the reducing agent is sodium metabisulfite.

23. The method of claim 22 wherein combining the mixture comprising the 2-methyl-1-(2-methylpropyl)-5-oxido-1H-imidazo[4,5-c][1,5]naphthyridine with an aqueous solution of sodium metabisulfite followed by an aqueous base comprises combining the mixture with an aqueous solution of 0.1 equivalent to 0.3 equivalent of sodium metabisulfite followed by a sufficient amount of aqueous base to adjust the mixture to a pH of greater than 10.

24. The method of claim 22 or claim 23 wherein combining the mixture comprising the 2-methyl-1-(2-methylpropyl)-5-oxido-1H-imidazo[4,5-c][1,5]naphthyridine with an aqueous solution of sodium metabisulfite followed by an aqueous base comprises combining six to ten milliliters of water per gram of 2-methyl-1-(2-methylpropyl)-5-oxido-1H-imidazo[4,5-c][1,5]naphthyridine with a mixture comprising eight to twelve milliliters of toluene per gram of 2-methyl-1-(2-methylpropyl)-5-oxido-1H-imidazo[4,5-c][1,5]naphthyridine.

25. The method of claim 24 wherein the volume ratio of water to toluene is 0.8:1.

26. The method of claim 20 wherein cooling the mixture comprises cooling the mixture to a temperature of 0° C. to 20° C.

27. The method of claim 14 wherein combining the 2-methyl-1-(2-methylpropyl)-1H-imidazo[4,5-c][1,5]naphthyridine with an oxidizing agent comprises combining the 2-methyl-1-(2-methylpropyl)-1H-imidazo[4,5-c][1,5]naphthyridine with at least one equivalent of peracetic acid.

28. The method of claim 14 wherein providing 2-methyl-1-(2-methylpropyl)-1H-imidazo[4,5-c][1,5]naphthyridine comprises:
   providing $N^4$-(2-methylpropyl)[1,5]naphthyridine-3,4-diamine in a carrier comprising a non-chlorinated solvent at a temperature of 18° C. to 30° C.;
   combining the $N^4$-(2-methylpropyl)[1,5]naphthyridine-3,4-diamine in the carrier with an organic acid to form a mixture;
   combining the mixture comprising the $N^4$-(2-methylpropyl)[1,5]naphthyridine-3,4-diamine and organic acid with a trialkyl orthoacetate at a temperature of 70° C. to 100° C.; and
   maintaining the temperature at 70° C. to 100° C. for a period of time sufficient to form 2-methyl-1-(2-methylpropyl)-1H-imidazo[4,5-c][1,5]naphthyridine.

29. The method of claim 28 wherein the organic acid is selected from the group consisting of p-toluenesulfonic acid, trifluoroacetic acid, ethanesulfonic acid, and mixtures thereof.

30. The method of claim 29 wherein the organic acid is p-toluenesulfonic acid.

31. The method of claim 28 wherein the trialkyl orthoacetate is triethyl orthoacetate.

32. The method of claim 28 wherein the non-chlorinated solvent is selected from the group consisting of toluene, butyl acetate, ethyl acetate, and combinations thereof.

33. The method of claim 32 wherein the non-chlorinated solvent is toluene.

34. The method of claim 28 further comprising cooling the mixture comprising 2-methyl-1-(2-methylpropyl)-1H-imidazo[4,5-c][1,5]naphthyridine to a temperature of 25° C. to 70° C.

35. The method of claim 28 wherein the 2-methyl-1-(2-methylpropyl)-1H-imidazo[4,5-c][1,5]naphthyridine is not isolated prior to combining it with the oxidizing agent.

36. The method of claim 28 wherein combining the $N^4$-(2-methylpropyl)[1,5]naphthyridine-3,4-diamine with an organic acid comprises combining the $N^4$-(2-methylpropyl)[1,5]naphthyridine-3,4-diamine with 0.02 equivalent to 0.08 equivalent of the organic acid.

37. The method of claim 28 wherein combining the mixture comprising the $N^4$-(2-methylpropyl)[1,5]naphthyridine-3,4-diamine and organic acid with a trialkyl orthoacetate comprises combining the mixture comprising the $N^4$-(2-methylpropyl)[1,5]naphthyridine-3,4-diamine and organic acid with at least one equivalent of the trialkyl orthoacetate.

38. The method of claim 28 wherein maintaining the temperature at 70° C. to 100° C. for a period of time sufficient to form 2-methyl-1-(2-methylpropyl)-1H-imidazo[4,5-c][1,5]naphthyridine comprises maintaining, the temperature at 70° C. to 100° C. for at least 30 minutes.

39. The method of claim 28 wherein providing $N^4$-(2-methylpropyl)[1,5]naphthyridine-3,4-diamine comprises:
   providing $N^4$-(2-methylpropyl)-3-nitro[1,5]naphthyridin-4-amine in a carrier comprising a non-chlorinated solvent;
   combining the $N^4$-(2-methylpropyl)-3-nitro[1,5]naphthyridin-4-amine in the carrier with a hydrogenation catalyst to form a mixture;
   subjecting the mixture comprising the $N^4$-(2-methylpropyl)-3-nitro[1,5]naphthyridin-4-amine and the hydrogenation catalyst to a hydrogen atmosphere under conditions effective to form $N^4$-(2-methylpropyl)[1,5]naphthyridine-3,4-diamine; and
   removing at least a portion of the hydrogenation catalyst from the $N^4$-(2-methylpropyl)[1,5]naphthyridine-3,4-diamine.

40. The method of claim 39 wherein the non-chlorinated solvent is selected from the group consisting of toluene, butyl acetate, ethyl acetate, and combinations thereof.

41. The method of claim 40 wherein the non-chlorinated solvent is toluene.

42. The method of claim 39 wherein combining the $N^4$-(2-methylpropyl)-3-nitro[1,5]naphthyridin-4-amine in the carrier with a hydrogenation catalyst comprises combining the $N^4$-(2-methylpropyl)-3-nitro[1,5]naphthyridin-4-amine in the carrier with a hydrogenation catalyst and isopropanol to form a mixture.

43. The method of claim 42 further comprising removing at least a portion of the isopropanol from the mixture of $N^4$-(2-methylpropyl)[1,5]naphthyridine-3,4-diamine in a carrier comprising toluene and isopropanol.

44. The method of claim 39 wherein the hydrogenation catalyst comprises platinum on carbon.

45. The method of claim 39 wherein the conditions effective to form $N^4$-(2-methylpropyl)[1,5]naphthyridine-3,4-diamine comprise a temperature of 15° C. to 30° C.

46. The method of claim 39 wherein the conditions effective to form $N^4$-(2-methylpropyl)[1,5]naphthyridine-3,4-diamine comprise a hydrogen pressure of $1 \times 10^5$ Pa to $3 \times 10^5$ Pa.

47. The method of claim 39 wherein the conditions effective to form $N^4$-(2-methylpropyl)[1,5]naphthyridine-3,4-diamine comprise a time period of at least 3 hours.

48. The method of claim 39 wherein the $N^4$-(2-methylpropyl)[1,5]naphthyridine-3,4-diamine is not isolated prior to combining it with the organic acid.

49. The method of claim 39 wherein providing $N^4$-(2-methylpropyl)-3-nitro[1,5]naphthyridin-4-amine comprises:
   providing 4-chloro-3-nitro[1,5]naphthyridine in a carrier comprising a water-miscible organic liquid;
   combining the 4-chloro-3-nitro[1,5]naphthyridine in the carrier with isobutylamine under conditions effective to form a mixture comprising $N^4$-(2-methylpropyl)-3-nitro[1,5]naphthyridine-4-amine;
   combining the mixture comprising the $N^4$-(2-methylpropyl)-3-nitro[1,5]naphthyridin-4-amine with water to form solid $N^4$-(2-methylpropyl)-3-nitro[1,5]naphthyridin-4-amine; and
   separating at least a portion of solid $N^4$-(2-methylpropyl)-3-nitro[1,5]naphthyridin-4-amine from at least a portion of the mixture comprising the water.

50. The method of claim 49 wherein the water-miscible organic liquid is selected from the group consisting of tetrahydrofuran, dichloromethane, acetonitrile, and mixtures thereof.

51. The method of claim 50 wherein the water-miscible organic liquid is tetrahydrofuran.

52. The method of claim 49 wherein the conditions effective to form a mixture comprising $N^4$-(2-methylpropyl)-3-nitro[1,5]naphthyridin-4-amine comprise a temperature of 15° C. to 30° C.

53. The method of claim 49 wherein combining the 4-chloro-3-nitro[1,5]naphthyridine with isobutylamine comprises combining the 4-chloro-3-nitro[1,5]naphthyridine with at least two equivalents of isobutylamine.

54. The method of claim 49 wherein separating at least a portion of the solid $N^4$-(2-methylpropyl)-3-nitro[1,5]naphthyridin-4-amine comprises filtering the solid $N^4$-(2-methylpropyl)-3-nitro[1,5]naphthyridin-4-amine.

55. The method of claim 54 further comprising washing and drying the solid $N^4$-(2-methylpropyl)-3-nitro[1,5]naphthyridin-4-amine.

56. The method of claim 49 wherein providing 4-chloro-3-nitro[1,5]naphthyridine comprises:
    providing 3-nitro[1,5]naphthyridin-4-ol in a carrier comprising N,N-dimethylformamide;
    combining the 3-nitro[1,5]naphthyridin-4-ol in the carrier with phosphorous oxychloride under conditions effective to form 4-chloro-3-nitro[1,5]naphthyridine;
    combining the mixture comprising the 4-chloro-3-nitro[1,5]naphthyridine with water under conditions effective to form solid 4-chloro-3-nitro[1,5]naphthyridine; and
    separating at least a portion of the solid 4-chloro-3-nitro[1,5]naphthyridine from at least a portion of the mixture comprising the water.

57. The method of claim 56 wherein the conditions effective to form 4-chloro-3-nitro[1,5]naphthyridine comprise a temperature of 15° C. to 35° C.

58. The method of claim 56 wherein the conditions effective to form 4-chloro-3-nitro[1,5]naphthyridine comprise a time period of at least one hour.

59. The method of claim 56 wherein the conditions effective to form solid 4-chloro-3-nitro[1,5]naphthyridine comprise cooling the mixture comprising the water to a temperature of less than 20° C.

60. The method of claim 56 wherein combining the 3-nitro[1,5]naphthyridin-4-ol with phosphorous oxychloride comprises combining the 3-nitro[1,5]naphthyridin-4-ol with at least one equivalent of phosphorous oxychloride.

61. The method of claim 56 wherein separating at least a portion of the solid 4-chloro-3-nitro[1,5]naphthyridine comprises filtering the solid 4-chloro-3-nitro[1,5]naphthyridine from the mixture comprising the water.

62. The method of claim 56 wherein separating at least a portion of the solid 4-chloro-3-nitro[1,5]naphthyridine occurs less than 30 minutes after combining the mixture comprising the 4-chloro-3-nitro[1,5]naphthyridine with water.

63. The method of claim 56 wherein the solid 4-chloro-3-nitro[1,5]naphthyridine is combined with isobutylamine within less than 4 hours of its preparation.

64. The method of claim 1 wherein providing 2-methyl-1-(2-methylpropyl)-5-oxido-1H-imidazo[4,5-c][1,5]naphthyridine comprises:
    providing 3-nitro-1,5-naphthyridin-4-ol in a carrier comprising N,N-dimethylformamide;
    combining the 3-nitro[1,5]naphthyridin-4-ol in the carrier with phosphorous oxychloride under conditions effective to form 4-chloro-3-nitro[1,5]naphthyridine;
    combining the mixture comprising the 4-chloro-3-nitro[1,5]naphthyridine with water under conditions effective to form solid 4-chloro-3-nitro[1,5]naphthyridine;
    separating at least a portion of the solid 4-chloro-3-nitro[1,5]naphthyridine from at least a portion of the mixture comprising the water;
    combining the separated solid 4-chloro-3-nitro[1,5]naphthyridine with a carrier comprising a water-miscible organic liquid;
    combining the 4-chloro-3-nitro[1,5]naphthyridine in the carrier with isobutylamine under conditions effective to form a mixture comprising $N^4$-(2-methylpropyl)-3-nitro[1,5]naphthyridin-4-amine;
    combining the mixture comprising the $N^4$-(2-methylpropyl)-3-nitro[1,5]naphthyridin-4-amine with water to form solid $N^4$-(2-methylpropyl)-3-nitro[1,5]naphthyridin-4-amine;
    separating at least a portion of solid $N^4$-(2-methylpropyl)-3-nitro[1,5]naphthyridin-4-amine from at least a portion of the mixture comprising the water; and
    converting the solid $N^4$-(2-methylpropyl)-3-nitro[1,5]naphthyridin-4-amine to 2-methyl-1-(2-methylpropyl)-5-oxido-1H-imidazo[4,5-c][1,5]naphthyridine.

65. A method of making $N^4$-(2-methylpropyl)-3-nitro[1,5]naphthyridin-4-amine, wherein the method comprises:
    providing 3-nitro[1,5]naphthyridin-4-ol in a carrier comprising N,N-dimethylformamide;
    combining the 3-nitro[1,5]naphthyridin-4-ol in the carrier with phosphorous oxychloride under conditions effective to form 4-chloro-3-nitro[1,5]naphthyridine;
    combining the mixture comprising the 4-chloro-3-nitro[1,5]naphthyridine with water under conditions effective to form solid 4-chloro-3-nitro[1,5]naphthyridine;
    separating at least a portion of the solid 4-chloro-3-nitro[1,5]naphthyridine from at least a portion of the mixture comprising the water;
    combining the separated solid 4-chloro-3-nitro[1,5]naphthyridine with a carrier comprising tetrahydrofuran;
    combining the 4-chloro-3-nitro[1,5]naphthyridine in the carrier with isobutylamine under conditions effective to form a mixture comprising $N^4$-(2-methylpropyl)-3-nitro[1,5]naphthyridin-4-amine;
    combining the mixture comprising the $N^4$-(2-methylpropyl)-3-nitro[1,5]naphthyridin-4-amine with water to form solid $N^4$-(2-methylpropyl)-3-nitro[1,5]naphthyridin-4-amine; and
    separating at least a portion of solid $N^4$-(2-methylpropyl)-3-nitro[1,5]naphthyridin-4-amine from at least a portion of the mixture comprising the water.

66. A method of making 2-methyl-1-(2-methylpropyl)-5-oxido-1H-imidazo[4,5-c][1,5]naphthyridine, the method comprising:
    providing 3-nitro[1,5]naphthyridin-4-ol in a carrier comprising N,N-dimethylformamide;
    combining the 3-nitro[1,5]naphthyridin-4-ol in the carrier with phosphorous oxychloride under conditions effective to form 4-chloro-3-nitro[1,5]naphthyridine;
    combining the mixture comprising the 4-chloro-3-nitro[1,5]naphthyridine with water under conditions effective to form solid 4-chloro-3-nitro[1,5]naphthyridine;
    separating at least a portion of the solid 4-chloro-3-nitro[1,5]naphthyridine from at least a portion of the mixture comprising the water;
    combining the separated solid 4-chloro-3-nitro[1,5]naphthyridine with a carrier comprising tetrahydrofuran;
    combining the 4-chloro-3-nitro[1,5]naphthyridine in the carrier with isobutylamine under conditions effective to form a mixture comprising $N^4$-(2-methylpropyl)-3-nitro[1,5]naphthyridine-4-amine;
    combining the mixture comprising the $N^4$-(2-methylpropyl)-3-nitro[1,5]naphthyridin-4-amine with water to form solid $N^4$-(2-methylpropyl)-3-nitro[1,5]naphthyridin-4-amine;
    separating at least a portion of solid $N^4$-(2-methylpropyl)-3-nitro[1,5]naphthyridin-4-amine from at least a portion of the mixture comprising the water combining the separated solid $N^4$-(2-methylpropyl)-3-nitro[1,5]naphthyridin-4-amine with a carrier comprising toluene;

combining the $N^4$-(2-methylpropyl)-3-nitro[1,5]naphthyridin-4-amine in the carrier with a hydrogenation catalyst and isopropanol to form a mixture;

subjecting the mixture comprising the $N^4$-(2-methylpropyl)-3-nitro[1,5]naphthyridine-4-amine and the hydrogenation catalyst to a hydrogen atmosphere under conditions effective to form $N^4$-(2-methylpropyl)[1,5]naphthyridine-3,4-diamine;

removing at least a portion of the hydrogenation catalyst from the $N^4$-(2-methylpropyl)[1,5]naphthyridine-3,4-diamine;

removing at least a portion of the isopropanol from the mixture of $N^4$-(2-methylpropyl)[1,5]naphthyridine-3,4-diamine in a carrier comprising toluene and isopropanol;

heating the $N^4$-(2-methylpropyl)[1,5]naphthyridine-3,4-diamine in the carrier to a temperature of 20° C. to 55° C.;

combining the $N^4$-(2-methylpropyl)[1,5]naphthyridine-3,4-diamine in the carrier with p-toluenesulfonic acid to form a mixture;

combining the mixture comprising the $N^4$-(2-methylpropyl)[1,5]naphthyridine-3,4-diamine and p-toluenesulfonic acid with a trialkyl orthoacetate at a temperature of 70° C. to 100° C.;

maintaining the temperature at 70° C. to 100° C. for a period time sufficient to form 2-methyl-1-(2-methylpropyl)-1H-imidazo[4,5-c][1,5]naphthyridine;

cooling the mixture comprising 2-methyl-1-(2-methylpropyl)-1H-imidazo[4,5-c][1,5]naphthyridine to a temperature of 45° C. to 55° C.;

combining the 2-methyl-1-(2-methylpropyl)-1H-imidazo[4,5-c][1,5]naphthyridine in the carrier with an oxidizing agent comprising peracetic acid to form a mixture;

maintaining the mixture comprising the 2-methyl-1-(2-methylpropyl)-1H-imidazo[4,5-c][1,5]naphthyridine and peracetic acid at a temperature of 45° C. to 55° C. for a period of time sufficient to form 2-methyl-1-(2-methylpropyl)-5-oxido-1H-imidazo[4,5-c][1,5]naphthyridine; and isolating at least a portion of the 2-methyl-1-(2-methylpropyl)-5-oxido-1H-imidazo[4,5-c][1,5]naphthyridine.

* * * * *